United States Patent [19]

Siegmund

[11] Patent Number: 4,588,294
[45] Date of Patent: May 13, 1986

[54] SEARCHING AND MEASURING ENDOSCOPE

[75] Inventor: Walter P. Siegmund, Pomfret Center, Conn.

[73] Assignee: Warner-Lambert Technologies, Inc., Morris Plains, N.J.

[21] Appl. No.: 625,149

[22] Filed: Jun. 27, 1984

[51] Int. Cl.⁴ .......................... G02B 23/26; A61B 5/00
[52] U.S. Cl. ..................................... 356/241; 356/237; 350/96.26; 128/634
[58] Field of Search .............................. 356/241, 237; 350/96.26, 507, 511, 558, 573, 512, 513; 128/634; 250/227

[56] References Cited

U.S. PATENT DOCUMENTS

| | | | |
|---|---|---|---|
| 3,520,587 | 7/1970 | Tasaki | 350/96.26 |
| 3,561,432 | 2/1971 | Yamaki | 356/241 |
| 3,877,779 | 4/1975 | Pierse | 350/513 |
| 4,267,828 | 5/1981 | Matsuo | 350/96.26 |

Primary Examiner—Vincent P. McGraw
Assistant Examiner—S. A. Turner
Attorney, Agent, or Firm—R. S. Strickler

[57] ABSTRACT

A searching and measuring endoscope employing two image-transmitting systems in a common housing. One system is fitted with a wide angle, fixed focus objective lens with large depth of field for searching and the other system is fitted with a narrow angle, fixed focus objective lens having a small depth of field and a predetermined working distance and magnification for measuring.

23 Claims, 7 Drawing Figures

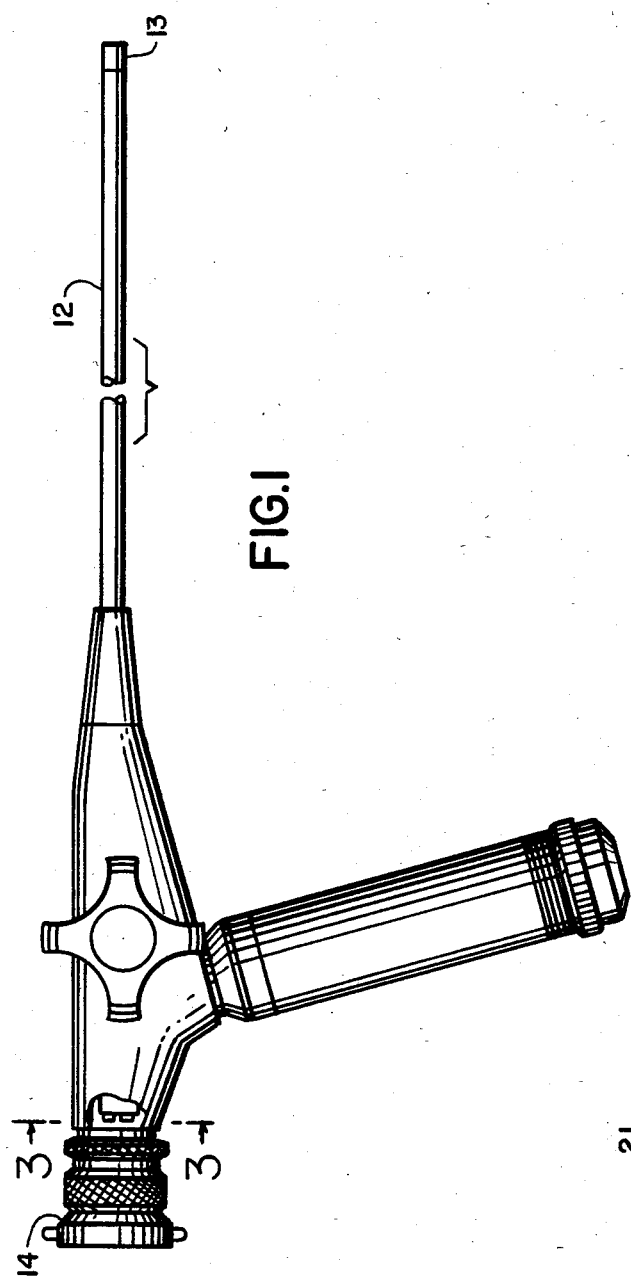
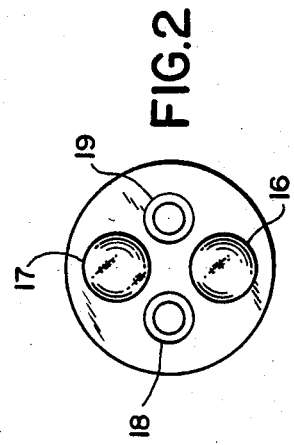
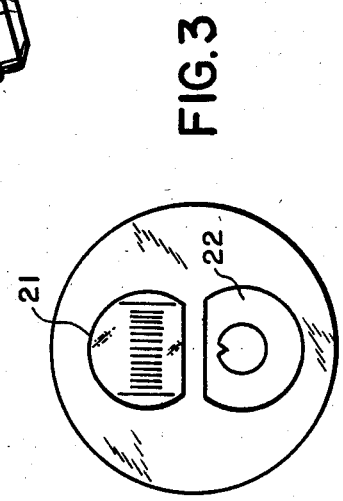

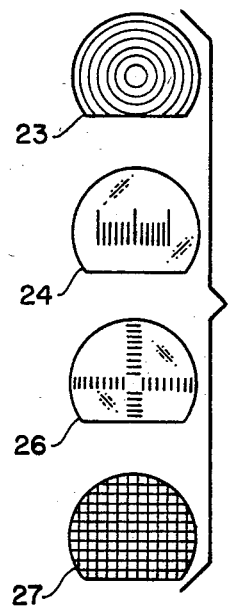
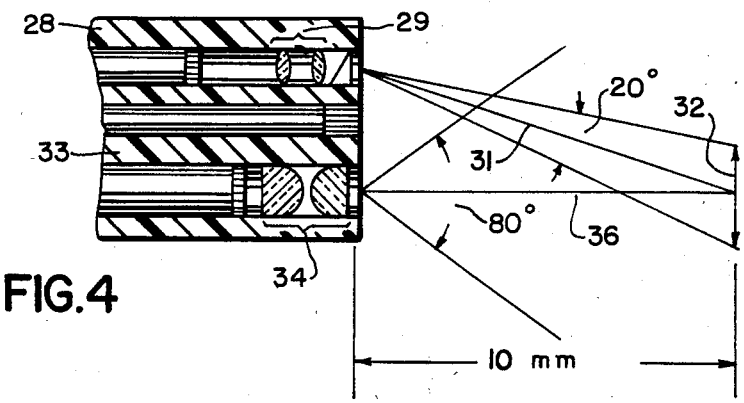
FIG.4
FIG.5
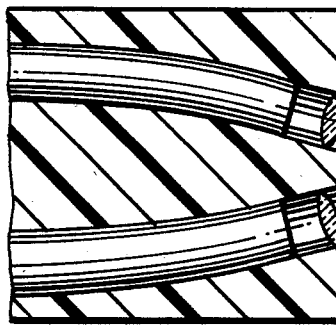
FIG.6
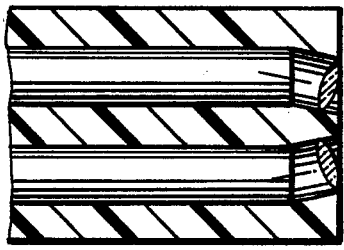
FIG.7

SEARCHING AND MEASURING ENDOSCOPE

BACKGROUND OF THE INVENTION

This invention relates to endoscopes useful to locate and observe flaws, cracks, imperfections or any other internal structures or objects in industrial, medical or veterinary situations located remotely relative to an observer.

These instruments may have more than one image-transmitting system for front viewing, i.e., directly ahead of the objective head, or lateral viewing, i.e., through the side of the objective head.

Such instruments may include various means for measuring the distance between an object and the objective lens.

Prior art devices are shown and described in U.S. Pat. Nos. 3,817,631, 3,819,267 and 4,279,247.

The '631 reference deals with measuring the distance of an object from the distal end of an endoscope by triangulating a pair of light beams directed through the scope to the object.

The '267 reference shows a complicated mechanical-optical means for viewing and measuring the actual size of an object by a combination of the measuring scheme of the '631 reference and a variable magnification lens system. Adjustment of these two systems applied to a differential element provides a resultant signal to an indicator means which is a relative indication of the actual size of the object.

The '247 reference discloses a plurality of image-transmitting systems within a common housing and a scheme for identifying each system for selective viewing.

SUMMARY OF THE INVENTION

In contrast to the prior art, the present invention provides a visual inspection unit embracing a simple dual image system for searching and measuring defects or imperfections in a remote object. The system requires no moving parts within the distal end or objective head.

A further feature of the invention is the provision of an inspection unit such as an endoscope useful for searching and measuring in a remotely located situation where the scope has at least one image-transmitting system fitted with a wide angle objective lens for searching and a second image-transmitting system fitted with a narrow angle objective lens of known magnification for measuring.

The present invention contemplates the use of either rigid optical lens trains or bundles of flexible fiber optics, as desired, for relaying the image to the eyepiece.

A still further feature of the invention is the provision of a search and measure inspection unit or endoscope which includes one or more reticles associated with one or both of the image-transmitting systems for reading the dimensions of an object according to meaningful and useful dimensional standards.

An inspection unit embracing certain principles of the present invention may comprise at least two image-transmitting systems each fitted with an objective lens at a distal end all enclosed in a common housing, a first image-transmitting system being fitted with a wide angle, fixed focus objective lens with corresponding large depth of field for searching and locating a critical area; and a second image-transmitting system being fitted with a narrow angle, fixed focus objective lens, said narrow angle lens having a relatively small depth of field and a relatively short, predetermined working distance and said second system having a predetermined magnification when in sharp focus while observing selected portions of said critical area.

Other features and advantages of the present invention will become more apparent from an examination of the succeeding specification when read in conjunction with the appended drawings, in which;

BRIEF DESCRIPTION OF THE DRAWINGS

FIG. 1 is a side elevation of a visual inspection unit incorporating the principles of the present invention;

FIG. 2 is a front elevation, somewhat enlarged, of the distal end of the unit of FIG. 1;

FIG. 3 is a view (enlarged) of the proximal ends of the image-transmitting trains showing a reticle and a mask;

FIG. 4 shows a series of reticle arrangements;

FIG. 5 is an optical diagram showing a typical spatial relationship between an object and an objective head when the narrow angle lens is in sharp focus; and FIGS. 6 and 7 show schematically how parallax can be overcome.

DESCRIPTION OF THE PREFERRED EMBODIMENT

Referring to FIGS. 1, 2, 3 and 4, the reference numeral 11 designates a visual inspection unit having a shaft 12, an objective head 13 and an eyepiece 14.

The shaft 12 houses two image-transmitting or relaying systems, not shown, one system being fitted at the distal end (see FIG. 2) with a relatively wide angle (ranging from 60° to 100°) lens 16 and the other system being fitted with a relatively narrow angle (ranging from 10° to 30°) lens 17.

The image-relaying means can take the form of a rigid optical train or a flexible fiber optics bundle.

The shaft 12 also includes one or more light guides 18 and 19.

Additional features may be included such as an articulation mechanism in the case of a flexible shaft and other utilities and accessories that are used commonly with endoscopes and the like.

FIG. 3 shows the proximal ends of the two image-transmitting systems with a masked reticle 21 at the end of the system having the narrow angle objective lens 17 and a plain mask 22 at the end of the system having the wide angle objective lens 16.

For purposes of claiming the invention, the narrow angle lens system may be referred to as the measuring system and the wide angle lens system may be referred to as the searching system.

For reasons that will become more apparent as the specification proceeds, the searching system may also be fitted with a mask inscribed with a reticle to present a coarse measurement while the measuring system reticle 21 provides a fine measurement.

FIG. 4 shows a variety of reticle configurations 23, 24, 26 and 27 which are merely representative of indicia that may be employed as dimensional indicators of the actual size of an observed object.

FIG. 5 shows an optical diagram demonstrating the principles of the invention. In this example, an image-transmitting fiber optics bundle 28 is fitted with a fixed focus objective lens 29 providing a relatively high magnification when in sharp focus and subtending a relatively narrow angle field of approximately 20° with an axis 31 intersecting an object 32 generating a predetermined working distance of 10 mm.

Alongside bundle 28 and within the same shaft 12, there is a second image-transmitting bundle 33 fitted with a fixed focus lens 34 providing a relatively low magnification and subtending a wide angle field of approximately 80° with an axis 36 intersecting the object 32 and the axis 31.

As is apparent in FIGS. 2 and 5, the diagram includes light guides 37 and 38 for reasons that are well known in the art.

The visual inspection system operates in searching a critical area and ultimately measuring a defect located in the critical area as follows:

The shaft of the inspection unit is inserted into a cavity of a machine (turbine housing, for example) or of an animate body (medical or veterinary situation) and the operator "searches" a remote area observing the area through eyepiece 14 which is common to both image-transmitting bundles 28 and 33. While viewing through the image bundle 33 equipped with the wide angle lens 34, the image will be in sharp focus over a wide range of distances. In general, the image through the narrow angle lens will appear blurred unless coincidentally the object is at the pre-set measuring distance. Having located a critical area, the operator advances or withdraws the shaft 12 until the point of interest or object (defect, flaw, imperfection, etc.) of the critical area comes into sharp focus in the image bundle 28 equipped with the narrow angle objective lens 29. The reticle on the image-transmitting bundle 28 is calibrated relative to the focal length of said narrow angle objective lens and said predetermined working distance such that when the narrow angle system is in sharp focus the actual size of the objects can be accurately measured.

FIGS. 6 and 7 show schematically objective head arrangements for overcoming parallax.

In FIG. 6 the image bundles are canted so that the centerlines of the optical axes intersect at the point of sharp focus while in FIG. 7 the lenses are offset to accomplish the same intersection.

It is anticipated that a wide variety of modifications may be devised in the present invention without departing from the spirit and scope thereof.

For example, individual eyepieces may be used, i.e., one for each image-transmitting system. The narrow angle lens system may be removable from the scope or inspection unit and inserted in a bore-scope, for example, having a spare channel. A reticle may be applied to both image-transmitting systems to effect a coarse and a fine measurement.

What is claimed is:

1. In a visual inspection unit of the type used to observe flaws, cracks, or other defects or imperfections of matter in industrial, medical or veterinary situations located remotely relative to an observer an assembly for searching and measuring comprising:
at least two image-transmitting systems each fitted with an objective lens at a distal end all enclosed in a common housing,
a first image-transmitting system being fitted with a wide angle, fixed focus objective lens with corresponding large depth of field for searching and locating a critical area; and
a second image-transmitting system being fitted with a narrow angle, fixed focus objective lens, said narrow angle lens having a relatively small depth of field and a relatively short, predetermined working distance and said second system having a predetermined magnification when in sharp focus while observing selected portions of said critical area.

2. The visual inspection unit of claim 1 where proximal ends of said image-transmitting systems are fitted with a common eyepiece through which the proximal ends of both systems are observable.

3. The unit of claim 2 in which the eyepiece is adjustable in focus to accommodate individual eye correction.

4. The unit of claim 1 in which each image-transmitting system is fitted with an adjustable focus eyepiece at the proximal end of each system.

5. The unit of claim 1 in which the proximal end of said second image-transmitting system is fitted with a reticle calibrated relative to said narrow angle and said predetermined working distance so that when said system is in sharp focus a physical dimension of said selected area can be observed and measured.

6. The unit of claim 5 in which the reticle represents a scale of polar coordinates, rectangular coordinates or a system of lines, grids or dots.

7. The unit of claim 1 in which the image-transmitting systems are spaced apart and disposed in a generally parallel relationship.

8. The unit of claim 1 in which the optical axes of the image-transmitting systems intersect one another at the point of sharp focus thereby eliminating parallax.

9. The unit of claim 7 in which one objective lens of one image-transmitting system is canted or displaced to eliminate parallax.

10. The system of claim 5 in which the proximal end of the first image-transmitting system is fitted with a reticle calibrated relative to said wide angle lens and said known distance so that when said narrow angle lens is in sharp focus the reticle on said first system represents a coarse measurement and the reticle on said second system represents a fine measurement of a flaw, crack or other imperfection observed.

11. The system of claim 1 in which the second image-transmitting system is separable from said first system and adapted to be removed readily from said housing.

12. The system of claim 1 in which the inspection unit is fitted with one or more light-transmitting fiber optic bundles to provide illumination.

13. The visual inspection unit of claim 1 in which the first and second image-transmitting systems are rigid optical lens trains.

14. The visual inspection unit of claim 1 in which one image-transmitting system includes one fiber optic image bundle.

15. The visual inspection unit of claim 1 in which both image-transmitting systems include flexible fiber optic image bundles susceptible of articulation.

16. The unit of claim 15 where proximal ends of said image bundles are fitted with a variable focus common eyepiece through which the proximal ends of both bundles are observable.

17. The unit of claim 15 in which the proximal end of said second bundle is fitted with a reticle calibrated relative to said narrow angle and said focus distance so that when said unit is moved into focus a physical dimension of said selected area can be observed.

18. The unit of claim 16 in which the reticle represents a scale of polar coordinates, rectangular coordinates or a system or lines, or dots.

19. The unit of claim 15 in which the image bundles are spaced apart and disposed in a generally parallel relationship.

20. The unit of claim 19 in which the centerlines of each bundle intersect one another at the point of sharp focus thereby eliminating parallax.

21. The unit of claim 16 in which the proximal end of the first image bundle is fitted with a reticle calibrated relative to said wide angle lens and said known distance so that when said narrow angle lens is in sharp focus the reticle on said first bundle represents a coarse reading and the reticle on said second bundle represents a fine reading.

22. The unit of claim 15 in which the second bundle is separable from said first bundle and adapted to be removed from said endoscope and inserted in a spare channel of a second endoscope.

23. The unit of claim 15 in which the endoscope is fitted with one or more light-transmitting fiber optic bundles.

* * * * *